US009730857B1

(12) United States Patent
Loya

(10) Patent No.: US 9,730,857 B1

(45) Date of Patent: Aug. 15, 2017

(54) MULTI-FUNCTIONAL STIMULATION DEVICE

(71) Applicant: Tia Loya, Hesperia, CA (US)

(72) Inventor: Tia Loya, Hesperia, CA (US)

(*) Notice: Subject to any disclaimer, the term of this patent is extended or adjusted under 35 U.S.C. 154(b) by 221 days.

(21) Appl. No.: 14/756,575

(22) Filed: Sep. 19, 2015

(51) Int. Cl.

*A61F 5/00* (2006.01)

*A61H 19/00* (2006.01)

(52) U.S. Cl.

CPC ............. *A61H 19/50* (2013.01); *A61H 19/32* (2013.01); *A61H 19/44* (2013.01); *A61H 2201/165* (2013.01); *A61H 2201/1692* (2013.01)

(58) Field of Classification Search

CPC ........ A61H 19/00; A61H 19/30; A61H 19/32; A61H 19/40; A61H 19/44; A61H 19/50; A61F 5/41; A61F 2005/411

USPC ...................................................... 600/38–41

See application file for complete search history.

(56) References Cited

U.S. PATENT DOCUMENTS

| | | | | |
|---|---|---|---|---|
| 5,690,603 | A | 11/1997 | Kain | 600/38 |
| 6,436,031 | B1 * | 8/2002 | Salib | A61F 5/41 600/39 |
| D618,361 | S | 6/2010 | Cannon et al. | D24/215 |
| 8,062,208 | B1 | 11/2011 | Cannon et al. | 600/38 |
| 8,974,369 | B2 | 3/2015 | Tomlinson, Jr. | 600/38 |
| 2005/0045674 | A1 | 3/2005 | Rehbein | 224/160 |
| 2013/0296645 | A1 * | 11/2013 | Evans | A61H 19/50 600/41 |
| 2014/0073851 | A1 | 3/2014 | Gioia | 600/38 |

FOREIGN PATENT DOCUMENTS

WO WO9100076 1/1991

* cited by examiner

*Primary Examiner* — John Lacyk

(74) *Attorney, Agent, or Firm* — C. J. Whewell

(57) ABSTRACT

Articles for providing synergistic, intense sensations of sexual pleasure for both partners engaging in intimate relations are provided. An article as provided herein is worn by a wearer and stimulates the sexual nerve synapses in the lower pelvic region of the users to simultaneously provide a near-ultimate sexual pleasure experience for each of the persons involved. The articles are washable, re-usable, and provide synergistic effects not conferred by any single article of manufacture ever contrived.

20 Claims, 6 Drawing Sheets

MULTI-FUNCTIONAL STIMULATION DEVICE

TECHNICAL FIELD

This invention relates generally to stimulation of the human central and peripheral nervous systems. More particularly, it relates to devices useful for stimulating nervous sensations in humans.

BACKGROUND OF THE INVENTION

The statements in this background section merely provide background information related to the present disclosure and may not constitute prior art.

Many archaeological digs have unearthed objects from times of antiquity which appear to have been used for various medical uses and for stimulating various parts of the human body. In some instances it appears that the purpose of some ancient artifacts was for stimulation of the sexual organs. Thus, the art or science of stimulating human genitalia spans much of recorded history.

Over the course of time various workers in different cultures have contrived many devices or articles for the purpose of stimulating or eliciting a sexual response in humans. The record of history shows that spheroids known as "Ben-wah Balls" have been known for hundreds of years. Since that time, many other contrivances and systems have been devised for stimulating a human sexual response.

It is accordingly a continuing goal for workers in this field of art to continuously seek new and better means for eliciting sexual responses and/or stimulation. As of this writing, the "sex toy" industry is a multiple-billion dollar per year sector of the global economy. By the present disclosure, the present invention provides new articles which are capable of providing an increased degree of stimulation in a synergistic fashion for two people of a pair who use the articles for the purpose of giving one another pleasurable sensations of high intensity.

SUMMARY OF THE INVENTION

This summary generally describes what the present disclosure provides, for some embodiments of a multi-functional stimulating device. A multi-functional stimulation device according to some embodiments comprises a substantially-cylindrical first stimulating member having a topside, an underside, a mid portion, a proximal end, and a distal end. The first stimulating member has an access opening that permits access to a hollow interior space within the first stimulating member. There is a second stimulating member that has a mid portion, a proximal end, and a distal end. There is a main bridge having a first end and a second end, with the first stimulating member being attached at its proximal end to the first end of the main bridge, the second stimulating member being attached at its proximal end to the second end of the main bridge. There is a lower aperture disposed between the first end of the main bridge and the proximal end of the first stimulating member, at the underside of the proximal end of the first stimulating member. There is also an upper aperture disposed between the first end of the main bridge and the proximal end of the first stimulating member, at the topside of the proximal end of the first stimulating member. The access opening is disposed between the upper aperture and the lower aperture.

BRIEF DESCRIPTION OF THE DRAWINGS

The drawings shown and described herein are provided for illustration purposes only and are merely exemplary of different embodiments provided herein, not intended to be construed in any delimitive fashion.

DETAILED DESCRIPTION

The following description is merely exemplary in nature and is in no way intended to limit the present disclosure, application, or uses.

Figure 1:
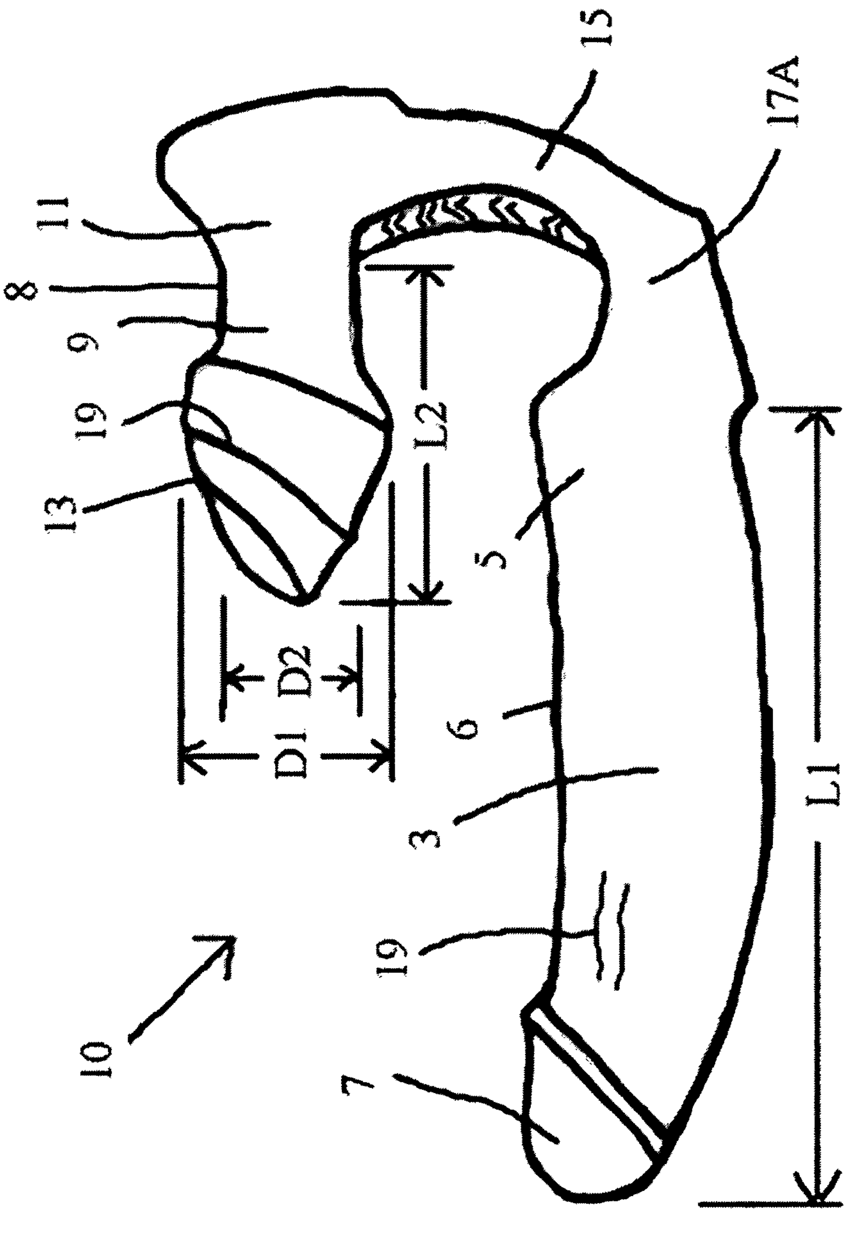
FIG. 1 is a side view of a stimulation device in accordance with some embodiments of the disclosure.

Referring now to the drawings, and initially to FIG. 1, there is shown a side view of a multi-functional stimulation device 10 according to this disclosure. Stimulating device 10 comprises a substantially linear first stimulating member 6, having a mid portion 3, a proximal end 5, and a distal end 7. There is a second stimulating member 8 which also has a mid portion 8, a proximal end 11 and a distal end 13. Disposed on the surfaces of the first stimulating member 6 and second stimulating member 8 are surface features 19, which in various embodiments can comprise any topographical features, such as one or any number more than one of ridges, raised areas, smooth areas, bumps, ribs and the like. In some embodiments, first stimulating member 6 is shaped, dimensioned, and contoured to be reminiscent of, and alternately an imitation of, any human male sexual organ (a.k.a. "penis"). In alternate embodiments, first stimulating member 6 can have essentially any outer shape or contour, subject to the proviso that it be dimensioned and configured to be inserted into any orifice of the human body that is capable of receiving, or dimensioned or configured to receive such first stimulating member 6. However, in general terms first stimulating member 6 is substantially cylindrical, given that it has an outer perimeter that is a quasi-circumference and a length dimension that is longer than its circumferential diameter when circular in cross section or quasi-circumferential largest diameter when not, and is generally not a perfectly right cylinder, but can have any selected degree of curvature along or of its centerline, as male sexual organs are generally so configured. Also shown in FIG. 1 is longest length dimension L1 of first stimulating member 6.

Second stimulating member 8 has a longest length dimension L2, a mid portion 9, a proximal end 11, and a distal end 13, and like first stimulating member 8, is in some embodiments substantially linear overall. In some embodiments, the distal end 13 of second stimulating member 8 is of a larger cross section or diameter as the case may be, than is mid portion 9. That is, the dimension D1 is greater than the dimension D2. In some embodiments both the distal end 13 and the mid portion 9 of the second stimulating member are circular in cross-section. However, it is within the scope of the present disclosure that either one or both of distal end 13 and mid portion 9 of the second stimulating member 8 are shaped other than circular in cross-section, including without limitation oblong, ovoid, or the shape of any regular or irregular polygon, including independent combinations of the foregoing. In some embodiments, D1 and D2 are dimensioned sufficiently so that if second stimulating member 8 is inserted into a human rectum, it becomes retained within the rectum, the anal sphincter being circumferentially disposed about and in substantial sealing engagement with mid portion 9 of second stimulating member 8, the distal end 13 of second stimulating member 8 acting as a barb within the rectum by virtue of D1 being sufficiently greater than D2 in cross section. Such features render stimulating device 10 as a whole, to be attachable to a human subject by such insertion, with no effort whatsoever thereafter being required by the person to whom such stimulating device 10 is so attached, for its continued attachment thereto. As used herein, orifice on a human subject includes the rectum and the vagina.

As shown in FIG. 1, there is a main bridge 15, which serves to attach or connect the proximal ends of the first stimulating member 6 and the second stimulating member 8 to one another. Generally, main bridge 15 is substantially linear, having a first end and a second end, and can have any geometric shape selected when viewed from the perspective of FIG. 2. In some non-limiting embodiments, main bridge 15 is rectangularly-shaped when viewed from the perspective of FIG. 2. In other non-limiting embodiments, main bridge 15 is trapezoidally-shaped when viewed from the perspective of FIG. 2. In other non-limiting embodiments, main bridge 15 is ovoid-shaped when viewed from the perspective of FIG. 2.

In some embodiments first stimulating member, main bridge 15, and second stimulating member 8 which provide a stimulating device 10 are all of unitary construction—that is, these elements are all present in a single molded article, stimulation device 10. Thus, in some embodiments, stimulating device 10 is comprised of a polymeric material.

Any polymeric material that is dermatologically-acceptable, pharmaceutically-acceptable or otherwise does not cause any deleterious reaction to occur in a person using stimulating device 10, such as any type of allergic reactions, is a suitable material from which a stimulating device 10 according to the disclosure may be provided. Such materials are typically flexible elastomers, and include neat polymers, and blends of polymers, including both thermoplastic resins and thermoset resins. Any one or more than one of the following are suitable: alpha olefin polymers, copolymers of alpha olefins, ethylene-vinyl acetate copolymers, vinyl polymers, synthetic and natural latex polymers, epoxy polymers, aliphatic or aromatic polyurethane polymers, aliphatic or aromatic polyurea polymers, fluorinated polymers including those sold under the trade name TEFLON® polymers, any selected silicone polymers, including without limitation tin-based silicone polymers and platinum-based silicone polymers. In alternate embodiments, first stimulating member 6 and second stimulating member 8 are comprised of materials other than polymeric materials, which can include without limitation wood, metals and any alloys of metals such as stainless steels, glass, and stone subject to the proviso that main bridging portion 15 is comprised of any flexible material configured to receive and maintain each of first stimulating member 6 and second stimulating member 8 in a configuration substantially as shown in the drawings figures of this application. In some embodiments, the polymeric material from which a stimulating device according to this disclosure is comprised, is a hypo-allergenic polymeric material.

In some embodiments, the length dimension L1 can be any length in the range of between 100 mm and 300 mm, and the length dimension L2 can be any length in the range of between 50 mm and 200 mm. In some embodiments within these ranges of parameters for L1 and L2, the ratio of L1/L2 is any ratio in the range of 1.0/1.0 to 3.0/1.0. The ranges specified above include all ranges within these ranges, and all values therebetween, and the values within the foregoing ranges for a given parameter can be selected independently of one another. In some embodiments, D1 is any value in the range of between 25 mm and 75 mm, including all values and ranges of values therebetween, and D2 is any value in the range of between 10 mm and 50 mm, including all values and ranges of values therebetween. The overall widest width of first stimulating member 6 that is analogous to D1 or D2, can be any selected value but is generally in the range of between 10 mm and 75 mm, including all values and ranges of values therebetween. In some embodiments, the outer contour of first stimulating member 6 is not uniform along its length L1, but can be varied as desired, or selected, by engineers to enhance any desired effect(s) of said stimulating device known to those of ordinary skill in the art of use of such devices.

Figure 2:
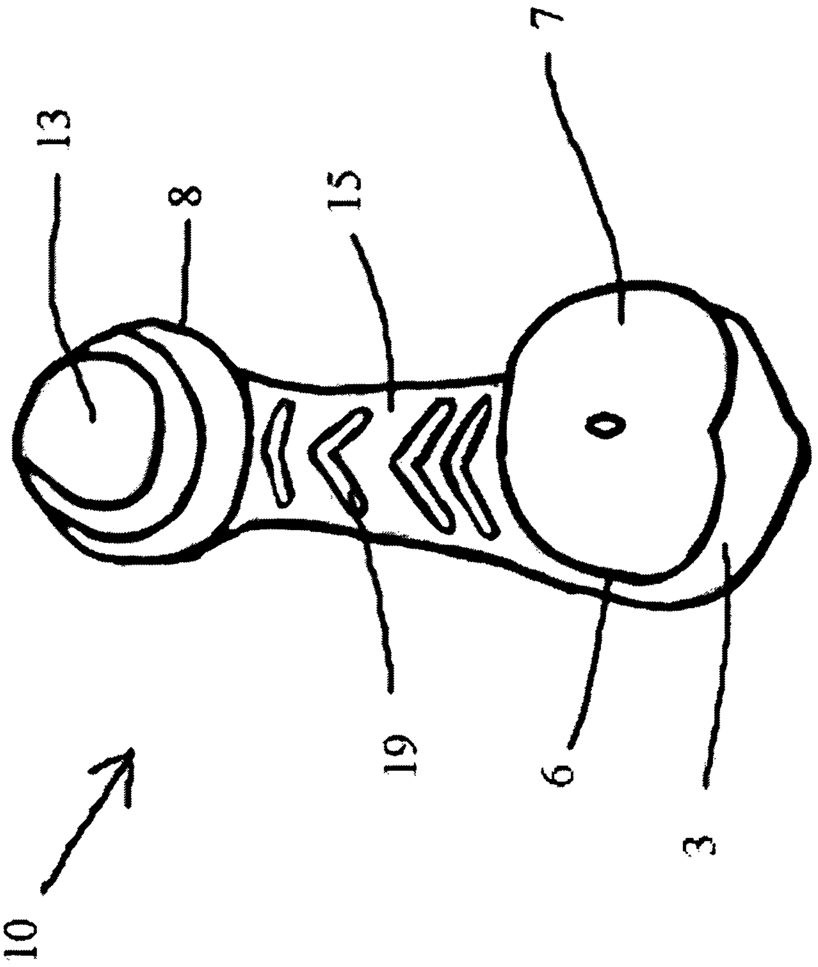
FIG. 2 is a frontal perspective view of a stimulation device in accordance with some embodiments of the disclosure.

FIG. 2 is a frontal perspective view of a stimulation device 10 in accordance with some embodiments of the disclosure, illustrating the respective locations of the first and second stimulating members, distal ends 7, 13, and main bridge 15. Main bridge 15 is shown as having surface features 19 present on its surface, which can be any surface feature as previously described.

Figure 3:
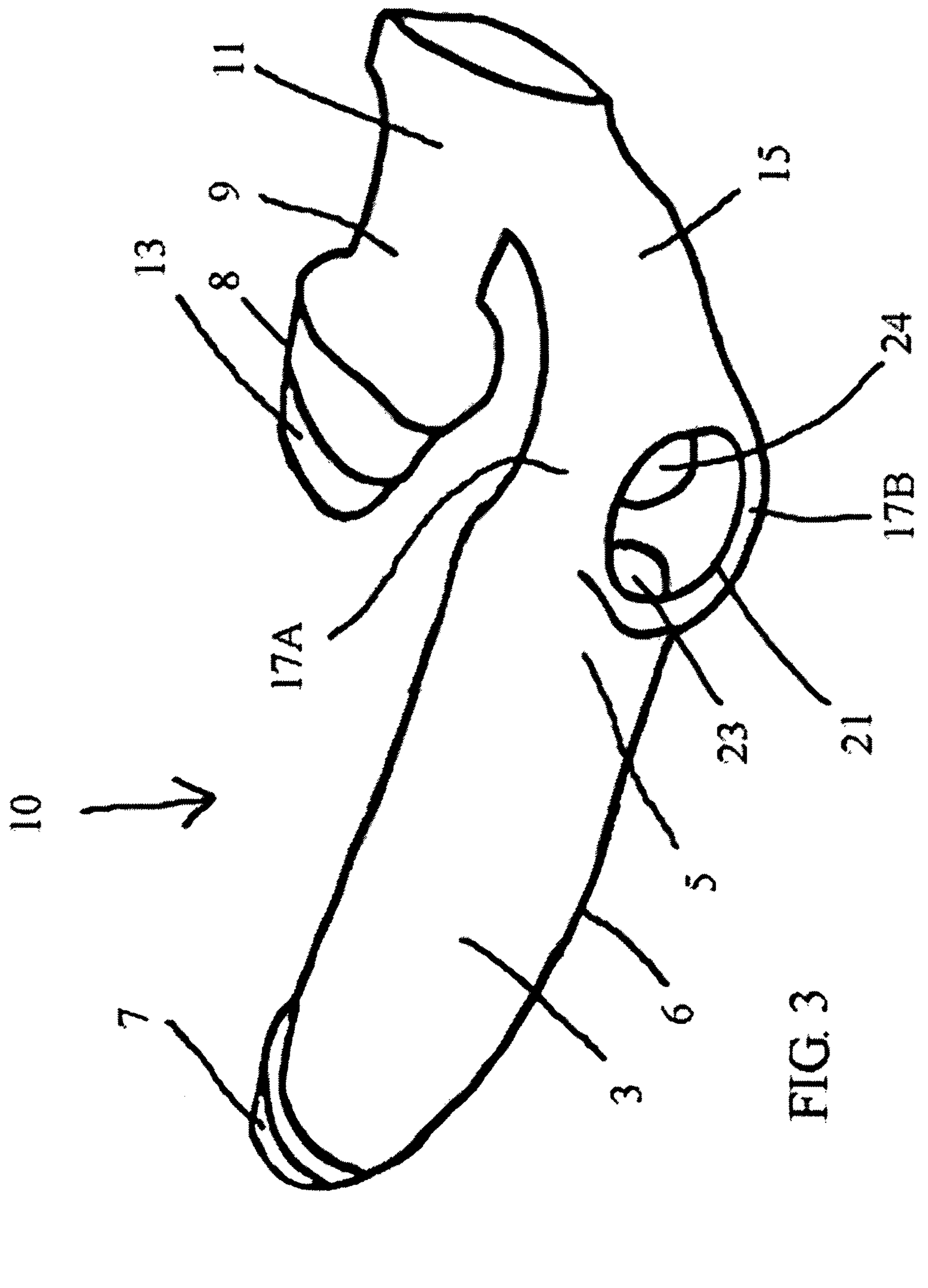
FIG. 3 is a lower rear perspective view of a stimulation device in accordance with some embodiments of the disclosure.

In FIG. 3 is shown a lower rear perspective view of a stimulation device 10 in accordance with some embodiments of the disclosure, showing the respective locations of mid portion 3, proximal end 5, distal end 7 of first stimulating member 6, and mid portion 9, proximal end 11, distal end 13 of second stimulating member 8. Main bridge 15 is shown, as well as lower aperture 21. Lower aperture 21 is an opening shaped and disposed substantially as shown, between the first end of main bridge 15 and the proximal end of first stimulating member 6 at the underside of first stimulating member 6. From the perspective view of FIG. 3 also seen is access opening 23 of hollow space 29 (FIGS. 4, 5), and upper aperture 24. First side bridge 17A and second side bridge 17B are also visible from this perspective view. In some embodiments, the perimeter of access opening 23 can be considered as substantially planar and defining a face, and the perimeters of upper aperture 24 and lower aperture 21 are each also substantially planar and define a face. In some embodiments, the face defined by access opening 23 is perpendicular to each of the faces of upper aperture 24 and lower aperture 21. In some embodiments, the face defined by access opening 23 makes an angle of any angle in the range of between 60 degrees and 120 degrees with either of the faces of upper aperture 24 and lower aperture 21. In some embodiments, the faces of upper aperture 24 and lower aperture 21 are substantially parallel to one another. As used herein, "substantially parallel", "substantially perpendicular" and "substantially planar" have their ordinary meanings and include embodiments where "substantially" means within a deviation of up to 20% of being either planar, perpendicular, or parallel. Perpendicular being defined as "at 90 degrees with respect to one another", 20% when applied to perpendicular means plus or minus 18 degrees either way. Planar is a 180 degree phenomenon, and substantially-planar includes any deviation from perfect planarity within plus or minus 36 degrees. Parallel is a 180 degree phenomenon, and substantially-parallel includes any deviation from being perfectly parallel within plus or minus 36 degrees. As applied to diameters or any other dimension mentioned herein, “substantially” means within 20% of the value being compared to. Substantially, when applied as a modifier also includes the condition it modifies, i.e., substantially planar includes the case of planarity.

Figure 4:
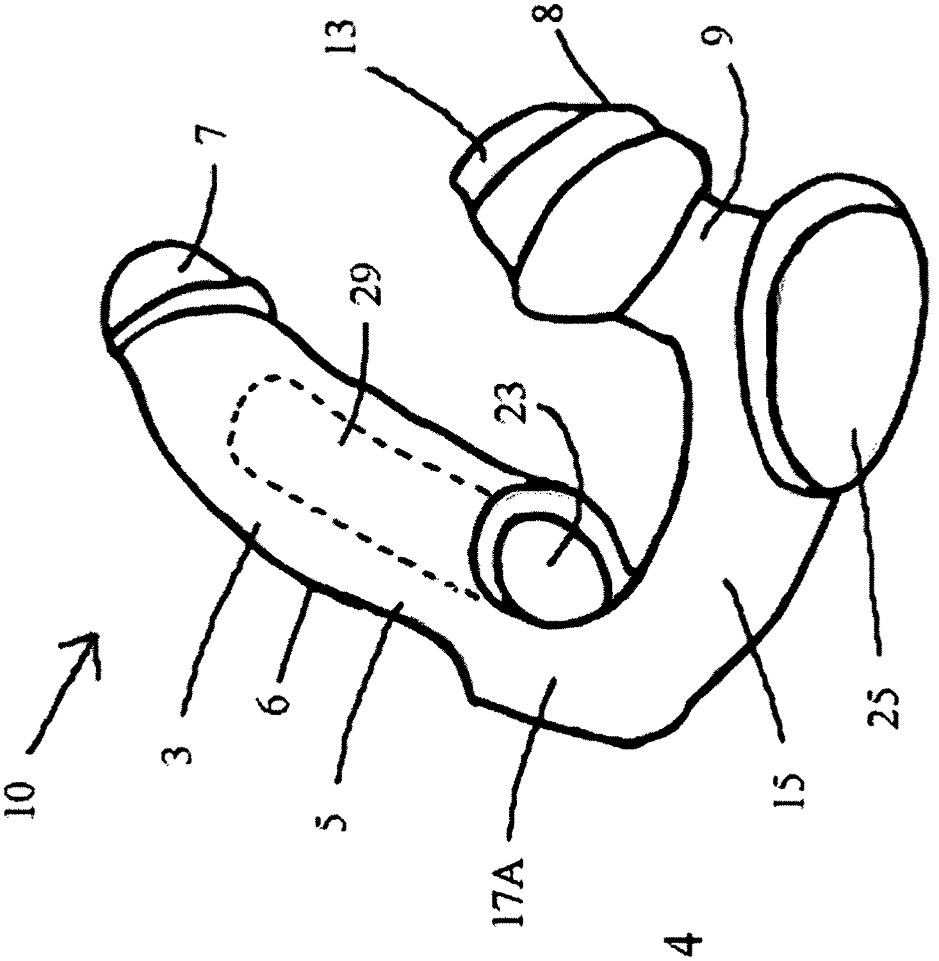
FIG. 4 is an upper rear perspective view of a stimulation device in accordance with some embodiments of the disclosure.

In FIG. 4 is shown an upper rear perspective view of a stimulation device 10 in accordance with some embodiments of the disclosure, illustrating many of the features shown and described with reference to FIG. 3 above, and additionally illustrating the presence of hollow space 29 present within first stimulating member 6. Hollow space 29 exists within first stimulating member 6 and is configured to receive the sexual organ of a human male subject, when inserted into hollow space access opening 23. The interior of hollow space 29 can be optionally configured to include surface features such as those described in reference to 19, to provide additional stimulation to a male sexual organ when present within hollow space 29. Also shown is the backside 25 of stimulation device 10 behind second stimulating member 8. In optional embodiments backside 25 is shaped as a suction cup so as to be removably attachable to any flat surface, as the configuration and use of suction cups is known to those of ordinary skill in the art.

Figure 5:
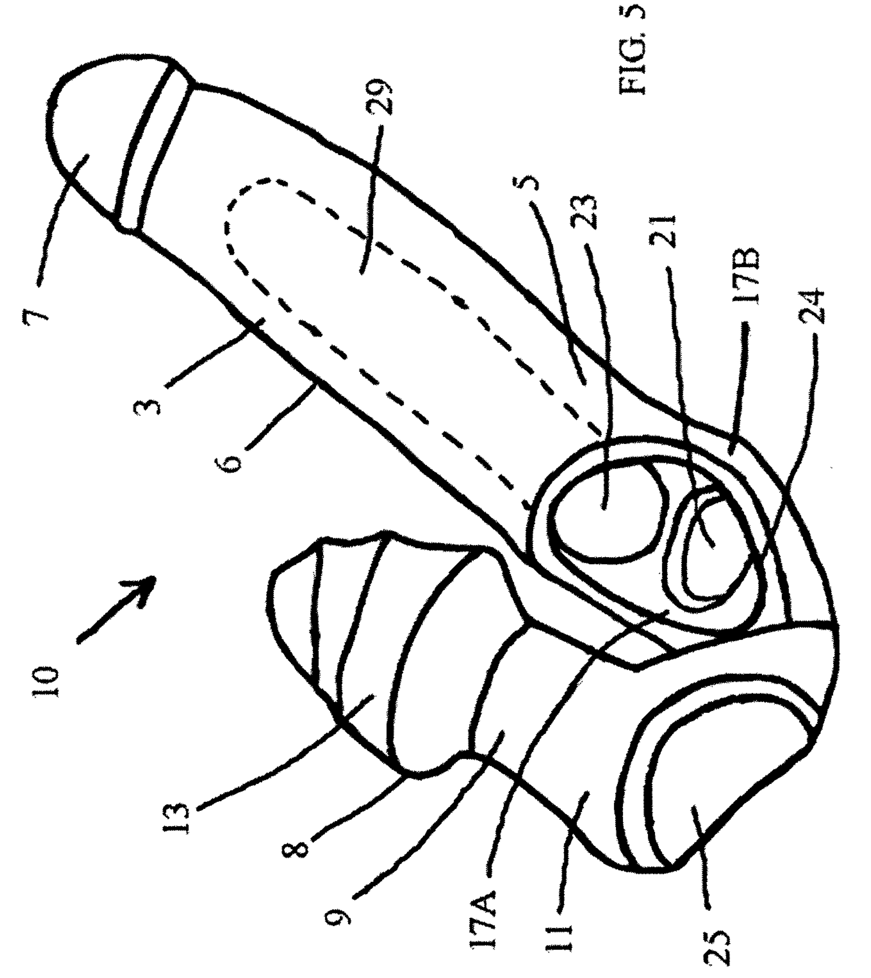
FIG. 5 is an alternate upper rear perspective view of a stimulation device in accordance with some embodiments of the disclosure.

In FIG. 5 is shown an alternate upper rear perspective view of a stimulation device 10 in accordance with some embodiments of the disclosure, illustrating the features shown and described with reference to FIGS. 3 and 4 above, showing their locations and configurations, including lower aperture 21, hollow space access opening 23, and upper aperture 24. Upper aperture 24 is an opening shaped and disposed substantially as shown, between the first end of main bridge 15 and the proximal end of first stimulating member 6 at the topside of first stimulating member 6.

From FIG. 5 it is evident that for some embodiments, first stimulating member 6 is attached to the remaining elements of stimulation device 10 by first side bridge 17A and second side bridge 17B, which side bridges are disposed adjacent to lower aperture 21. Stated another way, if one were to shear first side bridge 17A and second side bridge vertically in the view of FIG. 5, stimulation device 10 would separate into two pieces—the first stimulating member 6 and the remainder of device 10. In some embodiments, lower aperture 21 and upper aperture 24 are circular and are of the same diameter. In some embodiments when lower aperture 21 and upper aperture 24 are of the same diameter, their centerpoints are on the same axis and lower aperture 21 and upper aperture 24 define a cylinder having a length dimension that is the same as the height dimension of first side bridge 17A and second side bridge 17B. In some alternate embodiments, the diameter of lower aperture 21 is greater than the diameter of upper aperture 24. In other alternate embodiments, the diameter of lower aperture 21 is greater than the diameter of upper aperture 24. In other embodiments, either one or both of lower aperture 21 and upper aperture are ovoid-shaped, the longest interior measurement of an ovoid-shaped aperture when selected being akin or equivalent to a diameter for purposes of applying the foregoing descriptions of alternate embodiments which reference circular apertures having diameters, being applied to alternate embodiments when one or both of the lower aperture 21 and upper aperture 24 are ovoid-shaped.

A stimulating device 10 according to this disclosure is useful by members of any gender. In the case of subjects of the male gender desiring to use a stimulating device 10 of this invention, the person wears the device by inserting second stimulating member 8 into the rectum, passing their scrotal sack including testicles through lower aperture 21 (inserted from the direction of, and through upper aperture 24), and inserting their male sexual organ into hollow space 29. These steps of wearing stimulating device 10 can be undertaken by the user in any desired sequence. Once worn by a male subject, a synergistic level of stimulation is possible for both the wearer and their partner. The wearer can experience stimulation of their prostate area due to movement of main bridge 15 resulting from the typical motion associated with the act of intercourse caused by the movement of first stimulating member 6 during insertions or withdrawals from their partner, which cause main bridge 15 to rhythmically tug on second stimulating member 8, thereby stimulating the prostate and adjacent regions. Moreover, given embodiments for which stimulating device 10 is of unitary construction and is comprised of an elastomeric material, the circumferential region of lower aperture 21 simultaneously stimulates the scrotal region at its proximal location to the groin area, behaving simultaneously in analogous fashion to ancient “ring-type” sexual stimulation aids, now often referred to in the common vernacular as “cock rings” or “cock and ball rings.” A further attendant synergy is that the wearer’s male sexual organ is itself stimulated by virtue of being present within hollow space 29 and inherent movement it makes with respect to the interior thereof as a result of typical motion associated with the act of sexual intimacy. Finally, at the same time that all of the foregoing is happening, the wearer’s partner is themselves experiencing the typical sensations of the act of sexual intimacy, with the exception that the diameter of first stimulating member 6 has a greater circumference than the circumference of the male sexual organ of the wearer. The same is generally true with respect to the length L1 of first stimulating member 6. A stimulating device 10 of the disclosure can be used by persons not having an erect penis, and in some embodiments may eliminate the need for drugs such as VIAGRA® pills.

A stimulating device 10 according to this disclosure can also be worn in a useful manner by human females. Referring to U.S. Pat. No. 5,690,603 to Kain (the entire contents of which are herein incorporated by reference thereto), there is taught a stimulator having a bulb 324 that is inserted into a female’s vagina and retained therein by the wearer tightening their pubococcygeus or pelvic floor muscle(s), as in a Kegel exercise, the end 312 being reminiscent of a male sexual organ. A female subject wearing or using a device according to Kain (or similar devices, including without limitation those marketed under the tradename FEELDOE® stimulators) who desires to also use a stimulation device 10 according to this disclosure, can insert second stimulating member 8 into their rectum, and insert the end 312 of a Kain (or analogous portions of like devices) into hollow space 29 of stimulation device 10. Such a configuration or use provides anal stimulation to the wearer, and also provides their partner to be on the receiving end of a first stimulating member 6 having an external circumference that is larger than that provided by the Kain or similar or analogous device thereto being worn by the wearer in combination with a stimulating device 10 of this disclosure. The FEELDOE® and other like devices are commonly referred to as being a “dildo” in the vernacular.

Figure 6:
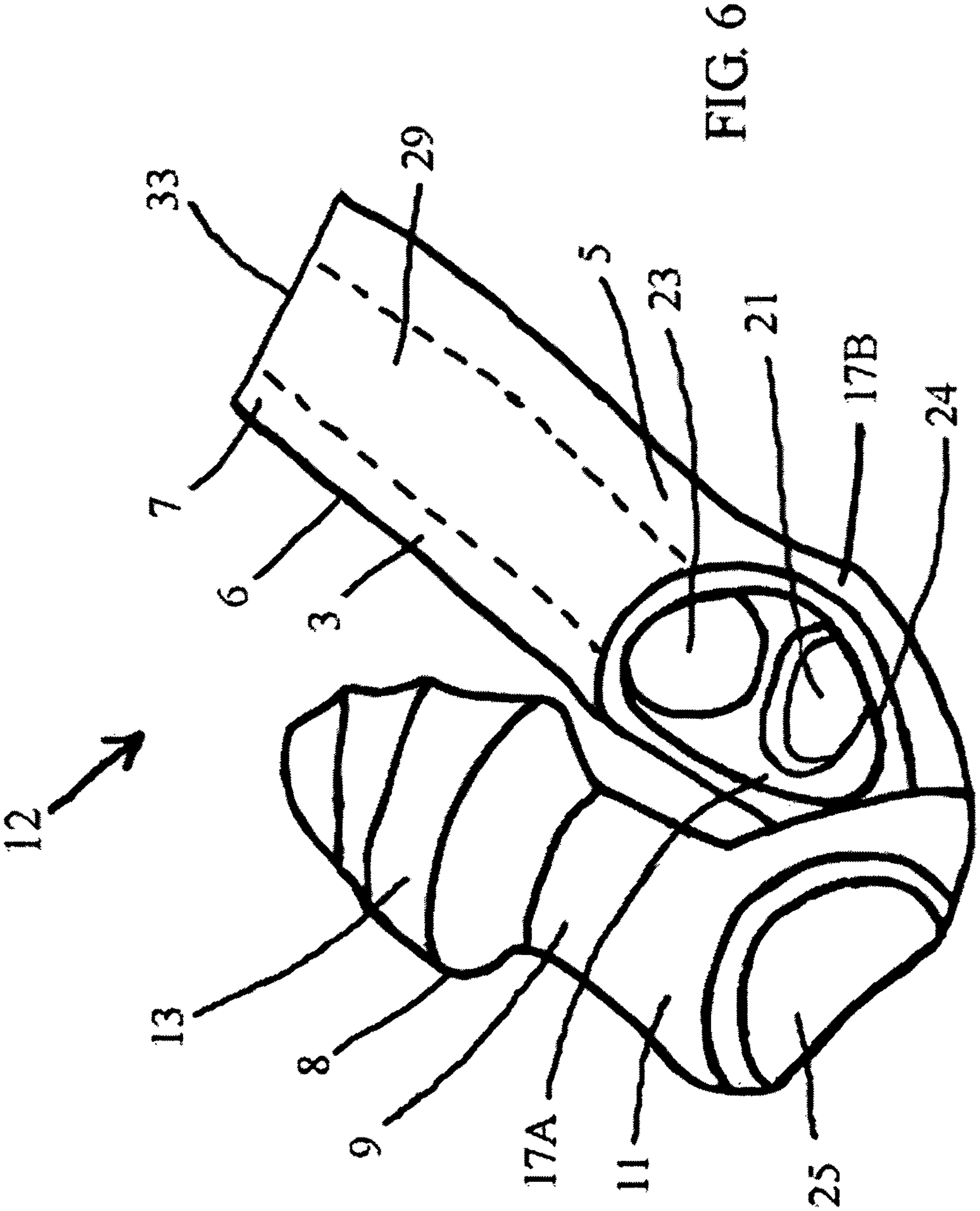
FIG. 6 is an alternate upper rear perspective view of a stimulation device in accordance with some embodiments of the disclosure.

In FIG. 6 is shown an alternate upper rear perspective view of a stimulation device 12 in accordance with some embodiments of the disclosure, illustrating the features shown and described with reference to prior-described embodiments, with the alternative feature of having a truncated distal end 7 that has an opening 33. Such feature enables a wearer of a stimulating device 12 according to this embodiment to insert their male sexual organ (or alternately a FEELDOE® device or like device) into opening 23, and to have the distal end ("head" or tip) of either their male sexual organ (or FEELDOE® device or like device) to protrude outside of and beyond the open distal end 7 of stimulating device 12. Such provision in the case of a male wearer of device 12 permits natural stimulation of the male sexual organ, and provides an alternate exterior profile when a FEELDOE® or like device is employed by a female wearer.

Consideration must be given to the fact that although this invention has been described and disclosed in relation to certain preferred embodiments, equivalent modifications and alterations thereof may become apparent to persons of ordinary skill in this art after reading and understanding the teachings of this specification, drawings, and the claims appended hereto. The present disclosure includes subject matter defined by any combinations of any one or more of the features provided in this disclosure with any one or more of any other features provided in this disclosure. These combinations include the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claims so modified. These combinations also include combination of the features and/or limitations of one or more of the independent claims with features and/or limitations of another independent claims to arrive at a modified independent claim, with the remaining dependent claims in their original text or as modified per the foregoing, being read and applied to any independent claim so modified. The present invention has been disclosed and claimed with the intent to cover modifications and alterations that achieve substantially the same result as herein taught using substantially the same or similar structures, being limited only by the scope of the claims which follow.

The invention claimed is:

1. A multi-functional stimulating device comprising:

a) a substantially-cylindrical first stimulating member having a topside, an underside, a mid portion, a proximal end, and a distal end, said first stimulating member having a hollow interior space with an access opening;

b) a second stimulating member having a mid portion, a proximal end, and a distal end;

c) a main bridge having a first end and a second end, said first stimulating member being attached at its proximal end to said first end of said main bridge, said second stimulating member being attached at its proximal end to said second end of said main bridge;

d) a lower aperture disposed between said first end of said main bridge and said proximal end of said first stimulating member, at said underside of said first stimulating member;

e) an upper aperture disposed between said first end of said main bridge and said proximal end of said first stimulating member, at said topside of said first stimulating member, said opening being disposed between said upper aperture and said lower aperture.

2. A stimulating device according to claim 1, wherein said upper aperture, said lower aperture, and said access opening each have a perimeter which defines a face, and wherein the face of said access opening is substantially perpendicular to at least one of the faces defined by the perimeters of said upper aperture and said lower aperture.

3. A stimulating device according to claim 1, wherein each of said first stimulating member and said second stimulating member each have a length dimension, and the ratio of the length of said first stimulating member to the length of said second stimulating member is any ratio in the range of between 1.0/1.0 to 3.0/1.0.

4. An apparatus according to claim 3, wherein the length dimensions of each of said first stimulating member and said second stimulating member are substantially parallel to one another.

5. A stimulating device according to claim 1, wherein said first stimulating member is configured and contoured to be reminiscent of an erect human male sexual organ.

6. A stimulating device according to claim 1 wherein at least one of said lower aperture and said upper aperture is ovoid-shaped.

7. A stimulating device according to claim 1 wherein said lower aperture and said upper aperture each have a diameter, and wherein the diameter of said lower aperture is greater than the diameter of said upper aperture.

8. A stimulating device according to claim 1 wherein said lower aperture and said upper aperture each have a diameter, and wherein the diameter of said upper aperture is greater than the diameter of said lower aperture.

9. A stimulating device according to claim 1 wherein said lower aperture and said upper aperture each have a diameter, and wherein the diameter of said upper aperture is substantially the same as the diameter of said lower aperture.

10. A stimulating device according to claim 1, which is comprised of a polymeric material that causes said stimulation device to substantially feel like a genuine male sexual organ as adjudged by a person touching said stimulating device.

11. A stimulating device according to claim 1 that is comprised of a hypo-allergenic polymeric material.

12. A stimulation device according to claim 1 configured to be worn by a male subject by their inserting their scrotum including testicles through said upper aperture and through said lower aperture, inserting said second stimulating member into their rectum, and inserting their male sexual organ into said hollow interior space through said access opening.

13. A stimulation device according to claim 1 wherein at least one of the exterior surface of said first stimulating member and the surface of said main bridge have a surface feature present thereon that is selected from the group consisting of: ridges, raised areas, smooth areas, bumps, and ribs.

14. A stimulation device according to claim 1 wherein the cross-sectional area of the distal end of said second stimulating member is of a greater cross-sectional area than the mid portion of said second stimulating member.

15. A stimulation device according to claim 1 wherein said distal end of said first stimulating member comprises an opening.

16. A multi-functional stimulating device comprising:

a) a first stimulating member shaped substantially as a human male sexual organ and having a topside, an underside, a mid portion, a proximal end, and a distal end, said first stimulating member having a hollow interior space with an access opening;

b) a second stimulating member having a mid portion, a proximal end, and a distal end;

c) a main bridge having a first end and a second end, said first stimulating member being attached at its proximal end to said first end of said main bridge, said second stimulating member being attached at its proximal end to said second end of said main bridge;

d) a lower aperture disposed between said first end of said main bridge and said proximal end of said first stimulating member, at said underside of said first stimulating member;

e) an upper aperture disposed between said first end of said main bridge and said proximal end of said first stimulating member, at said topside of said first stimulating member, said opening being disposed between said upper aperture and said lower aperture, said stimulation device being comprised of an elastomeric polymeric material of unitary construction.

17. A device according to claim 16 wherein said second stimulating member is configured to physically massage the prostate gland of a male wearer of said device, when said second stimulating member is present inside the wearer's rectum following insertion thereof therein.

18. A device according to claim 16 wherein said hollow interior space is configured to receive a male sexual organ.

19. A stimulation device according to claim 16 wherein said distal end of said first stimulating member comprises an opening.

20. A method for inducing orgasm in a human subject, comprising the steps of:

a) providing a device according to claim 15;

b) providing a first human subject as a wearer of said device;

c) inserting said second stimulating member into the rectum of said wearer;

d) inserting a member selected from the group consisting of: the male sexual organ of said wearer when said first human subject is male, and insertion of a dildo device present on said wearer when said first human subject is female;

e) providing a second human subject as receiver for said first stimulating member of said device; and f) repetitious insertion and withdrawal by said first human subject of said device into and out of a bodily orifice present on said second human subject, at any selected rhythm and rate within the discretion of said first human subject.

* * * * *